(12) United States Patent
Chung et al.

(10) Patent No.: US 8,597,924 B2
(45) Date of Patent: Dec. 3, 2013

(54) γ-BUTYROBETAINE HYDROXYLASE ORIGINATED FROM *NEUROSPORA CRASSA*

(75) Inventors: Sung Oh Chung, Bundang-gu Seongnam-si (KR); Bheonk-Uk Lee, Busan (KR); Whan-Koo Kang, Daejon (KR); Jae Yeong Ju, Seongnam-si (KR); Eun Sung Koh, Suwon-si (KR); Sung-Sik Park, Seoul (KR); Young-Hoon Park, Seongnam-si (KR)

(73) Assignee: CJ Cheiljedang Corporation, Seoul (KR)

(*) Notice: Subject to any disclaimer, the term of this patent is extended or adjusted under 35 U.S.C. 154(b) by 1467 days.

(21) Appl. No.: 10/590,831

(22) PCT Filed: Feb. 25, 2005

(86) PCT No.: PCT/KR2005/000532
§ 371 (c)(1),
(2), (4) Date: Oct. 11, 2007

(87) PCT Pub. No.: WO2005/083089
PCT Pub. Date: Sep. 9, 2005

(65) Prior Publication Data
US 2008/0050788 A1 Feb. 28, 2008

(30) Foreign Application Priority Data
Feb. 26, 2004 (KR) .................. 10-2004-0013032

(51) Int. Cl.
C12N 9/00 (2006.01)
C07H 21/02 (2006.01)
C07H 21/04 (2006.01)
C07K 1/00 (2006.01)
C07K 14/00 (2006.01)
C12P 21/06 (2006.01)

(52) U.S. Cl.
USPC .......... 435/183; 536/23.1; 536/23.2; 530/350; 435/69.1

(58) Field of Classification Search
USPC .......... 435/183, 69.1; 536/23.1, 23.2; 530/350
See application file for complete search history.

(56) References Cited

U.S. PATENT DOCUMENTS

2003/0037350 A1  2/2003  Glucksmann et al.

FOREIGN PATENT DOCUMENTS

WO  WO 2006/051387 A1  5/2006

OTHER PUBLICATIONS

Tabor et al., Proc Natl Acad Sci U S A. Feb. 1985 ;82(4):1074-8 A bacteriophage T7 RNA polymerase/promoter system for controlled exclusive expression of specific genes.*
Galagan et al., Nature. Apr. 24, 2003;422(6934):859-68.The genome sequence of the filamentous fungus *Neurospora crassa*.*
Cummings L, Riley L, Black L, Souvorov A, Resenchuk S, Dondoshansky I, Tatusova T. Genomic BLAST: custom-defined virtual databases for complete and unfinished genomes. FEMS Microbiol Lett. Nov. 5, 2002;216(2):133-8.*
NCBI genomic BLAST with microbial genomes 2005 pp. 1-11.*
Mims et al., Medical Microbiology Third EditionElsevier Science, 2004, pp. 280-282.*
Ziman et al., Mol Cell Biol. Jul. 1991;11(7):3537-44.Mutational analysis of CDC42Sc, a *Saccharomyces cerevisiae* gene that encodes a putative GTP-binding protein involved in the control of cell polarity.*
Miller et al Mol Cell Biol. Feb. 1994;14(2):1075-83.Cdc42p GTPase is involved in controlling polarized cell growth in *Schizosaccharomyces pombe*.*
Boyce et al J Bacteriol. Jun. 2001;183(11):3447-57. The CDC42 homolog of the dimorphic fungus *Penicillium marneffei* is required for correct cell polarization during growth but not development.*
Momany et al., Curr Opin Microbiol. Dec. 2002;5(6):580-5.Polarity in filamentous fungi: establishment, maintenance and new axes.*
Chen et al Eukaryot Cell. Jan. 2006;5(1):155-66.Cdc42 is required for proper growth and development in the fungal pathogen *Colletotrichum trifolii*.*
Hur et al, "Sequence-based screening for a Putative Y-Butyrobetaine Hydroxyylase Gene Form *Neurospora crassa*," J Microbiol Biotechnol (2006) 16(9), 1468-1471.
English Translation of Abstract: Japanese Publication No. JP S57-39791; Applicant: Sigma Tau Ind Farmaceuti; Published May 3, 1982 (Abstract Only) (1 PG).
English Translation of Abstract: Japanese Publication No. JP S57-39791; Applicant: Sigma Tau Ind Farmaceuti; Published May 3, 1982.
Frederic M.V. et al "Carnitine Biosynthesis: Identification of the CDNA Encoding Human Gamma-Butyrobetaine Hydroxylase," Biochemical and Biophysical Research Communications, (1998) vol. 250, pp. 50-510.
Bach A. "Carnitine Biosynthesis in Mammals" Reprod Nutr Dev, (1982) vol. 22(4) pp. 583-596.
Sandor A et al, "An Enzymatic Method for the Determination of Butyrobetaine Via Conversion to Carnitine After Isolation by High Performance Liquid Chromatography" Clin Chim Acta (1988) vol. 176(1) pp. 17-27.
Galagan et al, "The Genome Sequence of the Filamentous Fungus *Neurospora crassa*," Nature, (Apr. 2003) vol. 422, p. 859-868.

* cited by examiner

*Primary Examiner* — Maria Leavitt
(74) *Attorney, Agent, or Firm* — Casimir Jones SC

(57) ABSTRACT

Disclosed is a polynucleotide encoding γ-butyrobetaine hydroxylate (γ-BBH) originating from *Neurospora crassa*. Also disclosed are a recombinant vector comprising the polynucleotide, a transformant transformed with the recombinant vector, γ-BBH encoded by the polynucleotide, and a method of preparing L-carnitine, which comprises hydroxylating γ-butyrobetaine using γ-BBH encoded by the polynucleotide.

7 Claims, 3 Drawing Sheets

Lane 1 : Protein molecular size marker.
Lane 2 : E.coli BL21 w/o g -BBH gene.
Lane 3 : E.coli BL21 w/ g -BBH gene and induced by 1mM IPTG Lane1~4 : pT7-7 + g-BBH plasmid digested with Nde I
Lane 5: 1kb DNA ladder
Lane 6~9 : pT7-7 + g-BBH plasmid digested with Nde1 and Sal I

FIG. 3

CLUSTAL W (1.82) multiple sequence alignment

```
Human        --------MACTIQKAEALDGAHLMQILWYDEEESLYPAVWLRDNCPCSDCYLDSAKARK  52
rat          --------MHCAILKAEAVDGAPLMQIFWHDGAESLYPAVWLRDNCQCSDCYLHSAKARK  52
pseudomonas  NAIADVRTFPLISPLASAASFASGVSYTWADGRVSPFHNLWLRDNCPCGDCVYEVTREQV  60
N.crassa     --------MATAAVQVSVPAPVGQPDIGVAPDHQKVLARVKRRRENEKLESSLPPG----  48
                     :   ...  , ,: :    ,  : * :   :, Human        LLVEALDYNIGIKGLIFDRK-KVYITWPDEHVSEFQADWLKKRCFSKQARAKLQRELFFP 111
rat          LLLEALDVNIRMDDLTFDQK-KVYITWPNGHVSEFEANWLKKRCFSQEARAGLQGELFLP 111
pseudomonas  FLVADVPEDIQVQAVTIGDDGRLVVQWDDGHASAYHPGWLRAHAVDAQSLA--EREAARP 118
N.crassa     -FPRRLDSDLVWDGNTLAETYDWTVRLTEEAIDEIEAALRHFKSLNKPLGYINQETFPLP 107
              :    :  :      :      ,  ,,   ::, ,               *

Human        ECQYWGSELQLPTLDFEDVLRYDEHAYKWLSTLKKVGIVRLTGASDKPGEVSKLGKRMGF 171
rat          ECQYWGSELQLPTLNFEDVLNDDDHAYKWLSSLKKVGIVRLTGAADKRGEIIKLGKRIGF 171
pseudomonas  HKHRWMQGLSLPVYDHGAVMQDDDTLLEWLLAVRDVGLTQLHGVPTEPGALIPLAKRISF 178
N.crassa     RLHHTLRSLSHELHHGHGFKVLR--GLPVTSHTREENIIIVAGVSSHVAPIRGRQDNQ-H 164
               . :  *,      ,              :, .:  *, , , .   ,.

Human        LYLTFVGHTWQVQDKIDANNVAYTTGKLSFHTDYPALHHPPG-VQLLHCIKQTVTGGDSE 230
rat          LYLTFVGHTWQVQDKIDANNVAYTTGKLSFHTDYPALHHPPG-VQLLHCIKQTVTGGDSE 230
pseudomonas  IRESNFGVLFDVRSKADADSNAYTAFNLPLHTDLPTRELQPG-LQFLHCLVNDATGGNST 237
N.crassa     NGHPADVVLAHIKDLSTTVSDVSKIGAPAYTTEKQVFHTDAGDIVALFCLGEAAEGGQSY 224
                , ,::, :,, ,       *: ,, ,*:  *,*:   : ,.**:*

Human        IVDGFNVCQKLKKNNPQAFQILSS--TFVDFTDIGV-----DYCDFSYQSKHKIIELDDK 283
rat          IVDGFNVCQKLKEKNPQAFSILSS--TFVDFTDIGV-----DYCDFSYQSKHKIIELDDK 283
pseudomonas  FVDGFAIAEALRIEAPAAYRLLCE--TPVEFRNK--------DRHSDYRCTAPVIALDSS 287
N.crassa     LSSSWKVYNELAATRPDLVRTLAEPWVADEFGKEGRKFSVRPLLHFQSTAAAASREAKPE 284
              : ,,: : *    *  *,,    ,  :*   ,, Human        GQVVRINFNNATRDTIFDVP-VERVQPFYAALKEFVDLMN--SKESKFTFKMNPGDVITF 340
rat          GQVVRINFNNATRDTVFDVP-IERVQPFYAALKEFVDLMN--SKEYKYTFKMNPGDVITF 340
pseudomonas  GEVREIRLANFLR-APFQMD-AQRMPDVYLAYRRFIQMTR--EPRFCFTRRLEAGQLWCF 343
N.crassa     SERLIIQYARRTFTGVWGLPRSADIPPITEAQAEALDALHFTAEKYAVALDFRQGDVQFV 344
              .:  *, ,     : :    :     *  ,:   ,      ,,*::

Human        DNWRLLHGRRSYEAGTEISRHLEGAYAD----------------WDVYMS------RLRIL 379
rat          DNWRLLHGRRSYEAGTEISRHLEGAYAD----------------WDVYMS------RLRIL 379
pseudomonas  DNRRVLHARDAFDP-ASGDRHFQGCVYD----------------RDELLS------RILVL 381
N.crassa     NNLSVFHSRAGFRDEGEKQRHLVRLWLRDPENAWETPEALKERWERVYGGVSPEREVFPL 404
             :*  ::*,* ,:     , ,**:   :                : :,       ,: *

Human        RQRVENGN----------- 387
rat          RQRVMNGN----------- 387
pseudomonas  QR----------------- 383
N.crassa     EPQIRSASKGESVGTQGGGGY 425
```

(Sequences were aligned using the European Bioinformatics Institute (EMBL-EBI) sequence analysis program, clustalW.)

SEQUENCE LISTING

<160> NUMBER OF SEQ ID NOS: 4

<210> SEQ ID NO 1
<211> LENGTH: 1346
<212> TYPE: DNA
<213> ORGANISM: Neurospora crassa

<400> SEQUENCE: 1

```
atggccacgg cagcggttca ggtttcagtc ccagctccgg ttggacaacc agatatcggg      60
tacgctcctg accacgacaa gtacctcgca agagtcaaaa gacgacgaga aaacgagaag    120
ctggagtcgt ctcttccgcc aggtttccct cgaagactag actcggacct tgtgtgggac    180
ggcaacaccc tcgccgagac gtacgactgg acctacagac tgacagaaga ggccattgat    240
gaaatcgagg ccgcgcttcg tcattttaag agttagtaca gaatctctcc ttcctgtcct    300
tgggcatcaa gccatcaact aaccatcacc gcatgacagg cctcaacaag ccctaggct     360 acatcaacca agaaaccttc cccttcccc gcctacacca cactctccgc tccctctccc     420
acgagctcca ccacggccac ggcttcaaag tcctccgcgg gctccccgtc acctcccata    480
cacgcgagga aaacatcatc atctacgccg gcgtctcctc gcatgtcgct cctatccgcg    540
```

```
gccgccagga caaccagcac aacggccacc cagccgacgt agtcctagca cacatcaaag    600
acctgtccac gactgtttct gacgtgagca aaatcggtgc acccgcctac accaccgaga    660
aacaagtctt ccacaccgac gcaggcgaca tcgtcgccct cttttgcttg ggagaggccg    720
ccgagggcgg acagagttac ctgtccagca gctggaaggt gtacaacgag ctggcagcca    780
ctcggcccga tctggttcgc acgctggcgg agccgtgggt ggcggacgag tttggcaagg    840
aagggaggaa gttttctgtg cgaccgcttt tgcattttca gtctactgct gctgctgctt    900
ctagggaagc aaagcccgag tctgaacggc tcatcatcca gtacgcccgc cgcacgttta    960
cggggtattg gggattaccg aggtcggcgg atatcccgcc cattacggag gcgcaggcgg   1020
aggcgttgga tgcgctgcac tttacggcgg agaagtacgc ggtggcgctg gatttcaggc   1080 aggggatgt ccagtttgtg aataacttga gtgtgttcca ttcgagggcg gggtttagag   1140
atgaggggga gaagcagagg catttggtta ggttgtggtt gagagatccg gagaatgcgt   1200
gggagacgcc cgaggcgttg aaggaacggt gggaacgcgt gtatggcggg gtgagtccgg   1260
agagggaggt gtttccgctt gagccgcaga ttaggagcgc gagtaagggg gagagcgtgg   1320
ggacgcaggg tgggggaggg tattga                                         1346

<210> SEQ ID NO 2
<211> LENGTH: 425
<212> TYPE: PRT
<213> ORGANISM: Neurospora crassa

<400> SEQUENCE: 2

Met Ala Thr Ala Ala Val Gln Val Ser Val Pro Ala Pro Val Gly Gln
1               5                   10                  15

Pro Asp Ile Gly Tyr Ala Pro Asp His Asp Lys Tyr Leu Ala Arg Val
            20                  25                  30

Lys Arg Arg Arg Glu Asn Glu Lys Leu Glu Ser Ser Leu Pro Pro Gly
        35                  40                  45

Phe Pro Arg Arg Leu Asp Ser Asp Leu Val Trp Asp Gly Asn Thr Leu
    50                  55                  60

Ala Glu Thr Tyr Asp Trp Thr Tyr Arg Leu Thr Glu Glu Ala Ile Asp
65                  70                  75                  80

Glu Ile Glu Ala Ala Leu Arg His Phe Lys Ser Leu Asn Lys Pro Leu
                85                  90                  95

Gly Tyr Ile Asn Gln Glu Thr Phe Pro Leu Pro Arg Leu His Thr
            100                 105                 110

Leu Arg Ser Leu Ser His Glu Leu His His Gly His Gly Phe Lys Val
        115                 120                 125

Leu Arg Gly Leu Pro Val Thr Ser His Thr Arg Glu Glu Asn Ile Ile
    130                 135                 140

Ile Tyr Ala Gly Val Ser Ser His Val Ala Pro Ile Arg Gly Arg Gln
145                 150                 155                 160

Asp Asn Gln His Asn Gly His Pro Ala Asp Val Val Leu Ala His Ile
                165                 170                 175

Lys Asp Leu Ser Thr Thr Val Ser Asp Val Ser Lys Ile Gly Ala Pro
            180                 185                 190

Ala Tyr Thr Thr Glu Lys Gln Val Phe His Thr Asp Ala Gly Asp Ile
        195                 200                 205

Val Ala Leu Phe Cys Leu Gly Glu Ala Ala Glu Gly Gly Gln Ser Tyr
    210                 215                 220

Leu Ser Ser Ser Trp Lys Val Tyr Asn Glu Leu Ala Ala Thr Arg Pro
```

-continued

```
            225                 230                 235                 240
Asp Leu Val Arg Thr Leu Ala Glu Pro Trp Val Ala Asp Glu Phe Gly
                    245                 250                 255

Lys Glu Gly Arg Lys Phe Ser Val Arg Pro Leu Leu His Phe Gln Ser
                260                 265                 270

Thr Ala Ala Ala Ser Arg Glu Ala Lys Pro Glu Ser Glu Arg Leu
            275                 280                 285

Ile Ile Gln Tyr Ala Arg Arg Thr Phe Thr Gly Tyr Trp Gly Leu Pro
        290                 295                 300

Arg Ser Ala Asp Ile Pro Pro Ile Thr Glu Ala Gln Ala Glu Ala Leu
305                 310                 315                 320

Asp Ala Leu His Phe Thr Ala Glu Lys Tyr Ala Val Ala Leu Asp Phe
                325                 330                 335

Arg Gln Gly Asp Val Gln Phe Val Asn Asn Leu Ser Val Phe His Ser
                340                 345                 350

Arg Ala Gly Phe Arg Asp Glu Gly Glu Lys Gln Arg His Leu Val Arg
            355                 360                 365

Leu Trp Leu Arg Asp Pro Glu Asn Ala Trp Glu Thr Pro Glu Ala Leu
        370                 375                 380

Lys Glu Arg Trp Glu Arg Val Tyr Gly Gly Val Ser Pro Glu Arg Glu
385                 390                 395                 400

Val Phe Pro Leu Glu Pro Gln Ile Arg Ser Ala Ser Lys Gly Glu Ser
                405                 410                 415

Val Gly Thr Gln Gly Gly Gly Gly Tyr
            420                 425

<210> SEQ ID NO 3
<211> LENGTH: 35
<212> TYPE: DNA
<213> ORGANISM: Artificial sequence
<220> FEATURE:
<223> OTHER INFORMATION: Primer for amplifying tIle gene of gamma-
      butyrobetaine hydroxylase from Neurospora crassa

<400> SEQUENCE: 3
atgaattcca tatgatggcc acggcagcgg ttcag                              35

<210> SEQ ID NO 4
<211> LENGTH: 31
<212> TYPE: DNA
<213> ORGANISM: Artificial sequence
<220> FEATURE:
<223> OTHER INFORMATION: Primer for amplifying tIle gene of gamma-
      butyrobetaine hydroxylase from Neurospora crassa

<400> SEQUENCE: 4
attagtcgac tcaataccct cccccaccct g                                  31
```

γ-BUTYROBETAINE HYDROXYLASE ORIGINATED FROM *NEUROSPORA CRASSA*

TECHNICAL FIELD

The present invention relates to γ-butyrobetaine hydroxylase (γ-BBH) originating from *Neurospora crassa*. More particularly, the present invention relates to a polynucleotide encoding γ-butyrobetaine hydroxylase originating from *Neurospora crassa*, a recombinant vector comprising the polynucleotide, a transformant transformed with the recombinant vector, γ-butyrobetaine hydroxylase encoded by the polynucleotide, and a method of preparing L-carnitine by hydroxylating γ-butyrobetaine using γ-butyrobetaine hydroxylase encoded by the polynucleotide.

BACKGROUND ART

L-carnitine (3-hydroxy-4-trimethylamino-butyrate), which is also known as vitamin BT, is a natural vitamin analog that is very important in human metabolism. L-carnitine was originally isolated from bovine muscle tissue in 1905 by two Russian scientists, Gulewitsch and Krimberg, and its chemical structure was identified in 1932. L-carnitine is found in nearly all cells of the body and transports activated free long-chain fatty acids across the inner membrane of the mitochondria. Since the inner mitochondrial membrane is an impenetrable barrier to acyl-CoA esters, free long-chain fatty acids, activated to acyl-CoA esters in the cytoplasm, pass across the membrane when esterified to L-carnitine. When L-carnitine is present in low levels in the skeletal muscles, liver, heart and kidneys, free long-chain fatty acids are difficult to utilize as an energy source. This abnormal carnitine metabolism causes various diseases, including growth retardation, cardiomyopathy and muscle weakness. When L-carnitine is not synthesized in suitable amounts in the body, carnitine should be absorbed from foods to avoid carnitine deficiency symptoms. Especially in infants who are not able to biosynthesize L-carnitine, L-carnitine is an essential nutrient.

L-carnitine is used as an active component in pharmaceutical preparations. Exogenous supplementation of L-carnitine is required to treat carnitine deficiency and other diseases, especially cardiac diseases. Recently, this therapeutic use of L-carnitine has become increasingly important (R. A. Frenkel and J. D. Mc Garry; "Carnitine biosyntheis, metabolism and functions", Academic Press, 1980).

L-carnitine has been identified as playing many important roles in the body. However, conventional methods including biological extraction are not suitable for mass production of L-carnitine. One method capable of easily obtaining L-carnitine is to utilize DL-carnitine including optical isomers. This method causes side effects in the body because it contains D-carnitine (Curr. Ther. Res. 28, 195-198, 1980). In many cases, D-carnitine competes with L-carnitine in the body and interrupts the mitochondrial beta-oxidation of free long-chain fatty acids. In patients having remarkably reduced renal function, this impaired metabolism of long-chain fatty acids leads to more serious inhibition.

Many efforts have been made to obtain optically pure L-carnitine, which include a chemical optical resolution method (U.S. Pat. No. 5,166,426), a biological method using microorganisms or enzymes (U.S. Pat. No. 5,187,093), and a method of producing L-carnitine using a chiral compound as a starting compound (U.S. Pat. No. 6,420,599 B2).

Among various methods for obtaining L-carnitine, a biological method using microorganisms or enzymes employs a biological enzyme, gamma-butyrobetaine hydroxylase, to produce optically active L-carnitine. This enzyme was isolated in mice and humans (Rebouche and Engel, *J Biol Chem* 255:8700-8705, 1980), and its nucleotide sequence was identified. Higher organisms including mammals utilize an amino acid residue of proteins, lysine, as a precursor for L-carnitine biosynthesis, whereas *Neurospora crassa* produces optically pure L-carnitine from free lysine (Fraenkel, *Biol Bull*, 104: 359-371, 1953). The mechanism of L-carnitine biosynthesis is briefly as follows. Carnitine synthesis begins with methylation of lysine by S-adenosylmethionine acting as a methyl donor, resulting in the formation of ε-N-trimethyllysine. Trimethyllysine is enzymatically transformed into β-hydroxy-trimethyllysine. From the synthesized β-hydroxy-trimethyllysine, trimethylaminobutyl aldehyde is formed, and is then converted to γ-butyrobetaine.

A nucleotide sequence encoding γ-butyrobetaine hydroxylase, which is derived from *Neurospora crassa* and produces L-carnitine using γ-butyrobetaine, produced through the aforementioned mechanism, as a precursor, has not been identified prior to the present invention.

DISCLOSURE OF THE INVENTION

Based on this background, the present inventors identified a new gene encoding γ-butyrobetaine hydroxylase derived from *Neurospora crassa*, and successfully produced L-carnitine from γ-butyrobetaine by a biological method employing γ-butyrobetaine hydroxylase expressed using the gene.

BRIEF DESCRIPTION OF THE DRAWINGS

The above and other objects, features and other advantages of the present invention will be more clearly understood from the following detailed description taken in conjunction with the accompanying drawings, in which:

FIG. 3 is a multiple sequence alignment in which an amino acid sequence of γ-BBH from *Neurospora crassa* is aligned against that of human, rat and *Pseudomonas*-derived γ-BBH;

BEST MODE FOR CARRYING OUT THE INVENTION

Figure 1:
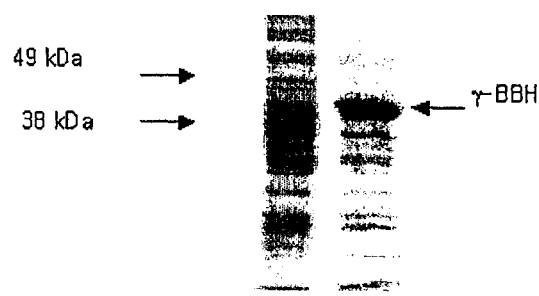
FIG. 1 shows the results of SDS-PAGE (polyacrylamide gel electrophoresis) of centrifugal supernatants of cell lysates of *Escherichia coli* (*E. coli*) BL21 not containing the γ-butyrobetaine hydroxylase (γ-BBH) gene and *E. coli* BL21 containing the γ-BBH gene and induced by IPTG (Isopropyl-β-D-thiogalactopyranoside)

In one aspect, the present invention provides a gene encoding γ-butyrobetaine hydroxylase derived from *Neurospora crassa*, the gene represented by SEQ ID NO. 1.

In order to obtain a gene encoding γ-butyrobetaine hydroxylase derived from the filamentous fungus *Neurospora crassa*, the present inventors first compared heterogeneous genes encoding γ-butyrobetaine hydroxylase to find conserved regions. A homology search was conducted between the conserved regions and the entire gene sequences of *N. crassa*, registered in the gene database. From genes having partially similar sequences, a candidate gene displaying γ-butyrobetaine hydroxylase activity was selected. In order to clone the candidate gene, primers specific for the gene were synthesized. A *Neurospora crassa* cDNA library was prepared and screened for the target gene using the synthesized primers. The thus obtained cDNA clone was inserted into a suitable vector. The resulting recombinant vector was transformed into *Escherichia coli*, and gene cloning was found to be successful by experiments using the transformant. Protein expression of the gene carried by the recombinant vector was induced by IPTG treatment and analyzed by SDS-PAGE. Compared to a control, an *E. coli* transformant displaying specific protein expression was found to produce L-carnitine using γ-butyrobetaine as a substrate (Table 1).

The present invention is based on the finding of a novel gene encoding γ-butyrobetaine hydroxylase derived from *Neurospora crassa*, the gene being identified as described above and being not identified prior to the present invention. A polynucleotide sequence of γ-butyrobetaine hydroxylase derived from *Neurospora crassa*, which has been newly identified by the present inventors, is represented by SEQ ID NO. 1.

Variants, for example, fragments and derivatives, of the polynucleotide of SEQ ID NO. 1 encoding a polypeptide having γ-butyrobetaine hydroxylase activity are also included within the scope of the present invention as long as they are expressed in a form containing a gene having the polynucleotide sequence of SEQ ID NO. 1.

In another aspect, the present invention provides a polynucleotide encoding a protein that has 70% or higher homology to the polynucleotide of SEQ ID NO. 1 and has γ-butyrobetaine hydroxylase activity.

The term "homology", as used herein for a polynucleotide sequence or a protein or polypeptide encoded by the polynucleotide sequence, indicates sequence similarity between wild-type amino acid sequences or wild-type nucleotide sequences. In the case of a protein, "homologous" includes an amino acid sequence 75% or higher, preferably 85% or higher, more preferably 90% or higher and even more preferably 95% or higher identical to the amino acid sequence of a γ-butyrobetaine hydroxylase protein according to the present invention. Typically, a protein homologue may include an active site identical to a target protein. In the case of a gene, "homologous" includes a gene sequence 75% or higher, preferably 85% or higher, more preferably 90% or higher and even more preferably 95% or higher identical to a polynucleotide sequence encoding a γ-butyrobetaine hydroxylase protein according to the present invention. The homology evaluation may be done with the naked eye or using a commercially available program. Using a commercially available computer program, the homology between two or more sequences may be expressed as a percentage (%), and the homology (%) between adjacent sequences may be evaluated.

In a preferred aspect, the present invention provides a polynucleotide encoding a protein that has a homology of 75% or higher, preferably 85% or higher, more preferably 90% or higher and even more preferably 95% to the sequence of SEQ ID NO. 1 and has γ-butyrobetaine hydroxylase activity.

In a further aspect, the present invention provides a polynucleotide encoding γ-butyrobetaine hydroxylase represented by SEQ ID NO. 2.

γ-butyrobetaine hydroxylase may be produced in a large scale according to the present invention by inserting a polynucleotide gene encoding γ-butyrobetaine hydroxylase derived from *Neurospora crassa* into a vector and inducing expression of the protein using the resulting recombinant vector.

Thus, in yet another aspect, the present invention provides a recombinant vector comprising a polynucleotide gene encoding γ-butyrobetaine hydroxylase derived from *Neurospora crassa*.

The term "vector", as used herein, refers to a DNA construct that contains a DNA sequence operably linked to regulatory sequences capable of controlling the expression of a protein in a suitable host and sequences introduced for facilitating other genetic manipulation or optimizing the expression of the protein. Such regulatory sequences include a promoter for transcription control, an operator selectively added for transcription control, a suitable mRNA ribosome binding site and sequences controlling termination of transcription/translation. Such a vector for insertion of an exogenous gene may be a plasmid, a virus, a cosmid, or the like.

The vector includes cloning vectors and expression vectors. The cloning vector is a replicable plasmid into which exogenous DNA is inserted, and delivers exogenous DNA into host cells transformed therewith. "Expression vector" typically means a carrier into which a fragment of exogenous DNA, generally a fragment of double-stranded DNA, is inserted. "Exogenous DNA" refers to heterogeneous DNA that does not naturally occur in host cells. The expression vector is able to replicate independently of host chromosomal DNA in host cells so that inserted exogenous DNA may be produced. As generally known in the art, in order to increase the expression level of a transfected gene in a host cell, the gene should be operably linked to transcription and translation regulatory sequences functional in a host cell selected as an expression system.

A pT7-BBH2 vector (*Eshcherichia coli* DH5α CJ2004), which is constructed according to the present invention for expression of a polynucleotide encoding γ-butyrobetaine hydroxylase derived from *Neurospora crassa*, was deposited at an international depository authority; the Korean Culture Center of Microorganisms (KCCM) on Jan. 27, 2004, and assigned accession number KCCM-10557.

In still another aspect, the present invention provides a transformant transformed with a recombinant vector comprising the gene.

The term "transformation", as used herein, means the introduction of DNA into a suitable host cell so that the DNA is replicable, either as an extrachromosomal element, or by chromosomal integration. Host cells useful for the transformation according to the present invention may be prokaryotic or eukaryotic. In addition, host cells having high introduction efficiency of foreign DNA and having high expression levels of introduced DNA may be typically used. Examples of host cells include prokaryotic and eukaryotic cells, such as bacteria, for example, *Escherichia* sp., *Pseudomonas* sp., *Bacillus* sp. and *Streptomyces* sp., fungi and yeast, insect cells such as *Spodoptera frugiperda* (Sf9), and animal cells such as CHO, COS 1, COS 7, BSC 1, BSC 40 and BMT 10. *Escherichia coli* maybe preferably used.

An amino acid sequence encoded by the polynucleotide of SEQ ID NO. 1 is represented by SEQ ID NO. 2. Thus, in still another aspect, the present invention provides γ-butyrobetaine hydroxylase derived from *Neurospora crassa* and having the amino acid sequence of SEQ ID NO. 2.

In still another aspect, the present invention provides γ-butyrobetaine hydroxylase selected from the group consisting of variants that have a homology of 75% or higher, preferably 85% or higher, more preferably 90% or higher and even more preferably 95% to the sequence of SEQ ID NO. 2 and have γ-butyrobetaine hydroxylase activity.

Figure 5:
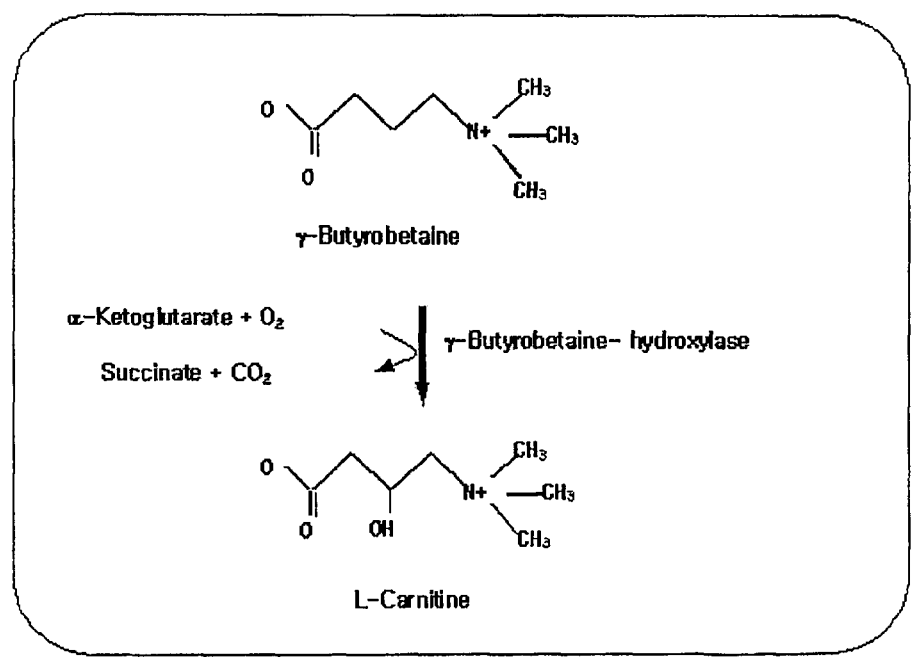
FIG. 5 is a schematic diagram of a process of producing L-carnitine from γ-butyrobetaine.

As shown in FIG. 5, the γ-butyrobetaine hydroxylase according to the present invention may be used to produce L-carnitine from γ-butyrobetaine, thereby obtaining optically pure L-carnitine.

Thus, in still another aspect, the present invention provide a method of preparing L-carnitine which comprises hydroxylating γ-butyrobetaine using the aforementioned γ-butyrobetaine hydroxylase.

The L-carnitine obtained as described above may be used for L-carnitine supplementation for treating carnitine deficiency and other therapeutic purpose.

A better understanding of the present invention may be obtained through the following examples which are set forth to illustrate, but are not to be construed as the limit of the present invention.

EXAMPLE 1

Construction of *Neurospora crassa* cDNA Library

In order to obtain cDNA of *Neurospora crassa*, mRNA was first isolated from *Neurospora crassa*, and cDNA was synthesized from the isolated mRNA by PCR (Polymerase Chain Reaction) using a polyT primer. cDNA was inserted into ECoRI/XhoI sites of an AD5 cloning vector, and a cDNA pool constructed in a plasmid was prepared as follows. An *Escherichia coli* strain BNN322 was cultured in LB medium supplemented with kanamycin and 0.2% maltose overnight, harvested by centrifugation, and suspended in 1 ml of 10 mM $MgSO_4$. The bacterial suspension was cultured with $3.5 \times 10^7$ λ phages possessing a cDNA pool for 30 min at 30° C. without agitation. After 2 ml of LB medium was added to the culture, the infected strain was cultured for 60 min at 30° C. with agitation. The resulting culture was smeared onto LB plates containing ampicillin (75 μl/ml). Plasmids were isolated from emerged colonies, thus creating a cDNA library pool.

EXAMPLE 2

Preparation of Primers for Obtaining γ-butyrobetaine Hydroxylase Gene

The amino acid sequence of *Neurospora crassa*-derived γ-butyrobetaine hydroxylase (γ-BBH) was compared with that of human, rat and *Pseudomonas*-derived γ-BBH (FIG. 3). Sequence 1 represents the amino acid sequence of *N. crassa*-derived γ-BBH, Sequence 2 for that of human-derived γ-BBH, Sequence 3 for that of rat-derived γ-BBH, and Sequence 4 for that of *Pseudomonas*-derived γ-BBH. Sequence homology results are as follows (Start of Pairwise alignments):

Sequences (1:2) Aligned. Score: 11%
Sequences (1:3) Aligned. Score: 11%
Sequences (1:4) Aligned. Score: 10%
Sequences (2:3) Aligned. Score: 88%
Sequences (2:4) Aligned. Score: 29%
Sequences (3:4) Aligned. Score: 29%.

*N. crassa*-derived γ-BBH was found to have a 11% homology to human-derived γ-BBH.

A set of primers, below, was designed for cloning *N. crassa*-derived γ-BBH based on sequence information of *N. crassa* genome.

```
Primer 1 (SEQ ID NO. 3):
5'- ATG AAT TCC ATA TGA TGG CCA CGG CAG CGG TTC

AG -3'

Primer 2 (SEQ ID NO. 4):
5'- ATT AGT CGA CTC AAT ACC CTC CCC CAC CCT G -3'
```

EXAMPLE 3

Obtainment of γ-BBH-encoding Gene

The γ-BBH gene was amplified from the *Neurospora crassa* cDNA library, prepared in Example 1, by PCR using a set of primers prepared in Example 2. The PCR product was electrophoresed on an agarose gel, and a band was observed at about 1.4 kb. The nucleotide sequence of the amplified gene was determined by automatic DNA sequencing. Also, the determined nucleotide sequence was subjected to homology searches for nucleotide sequences using the BLAST program from NCBI. As a result, a gene 100% identical to the amplified gene was found in the genome sequence of *Neurospora crassa*, and the found gene was mentioned for function of its translational product only as a hypothetical protein. Then, the PCR product was digested with both EcoRI and SalI, ligated with pUC19 digested with the same restriction enzymes, and introduced into *Escherichia coli* DH5. A transformant was identified by blue/white screening. When the plasmid was isolated from the transformant and analyzed, the γ-butyrobetaine hydroxylase gene was found to have been successfully inserted into the plasmid.

EXAMPLE 4

Construction of pT7-BBH2 Plasmid

Figure 2:
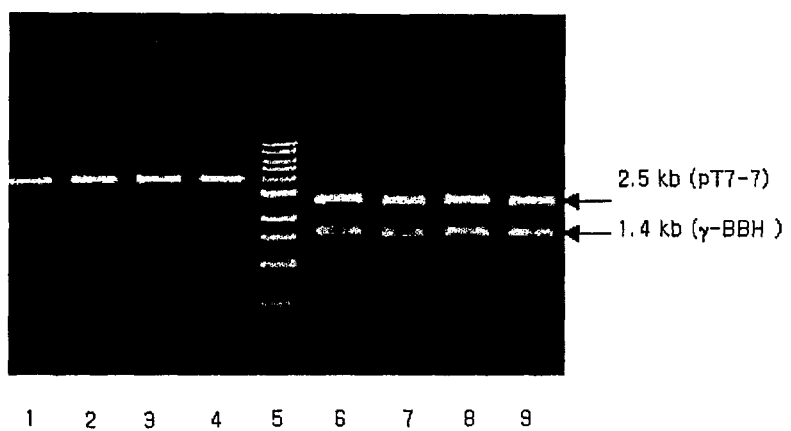
FIG. 2 shows the results of 0.8% agarose gel electrophoresis of an amplified γ-BBH cDNA gene cloned into pT7-7.
Figure 4:
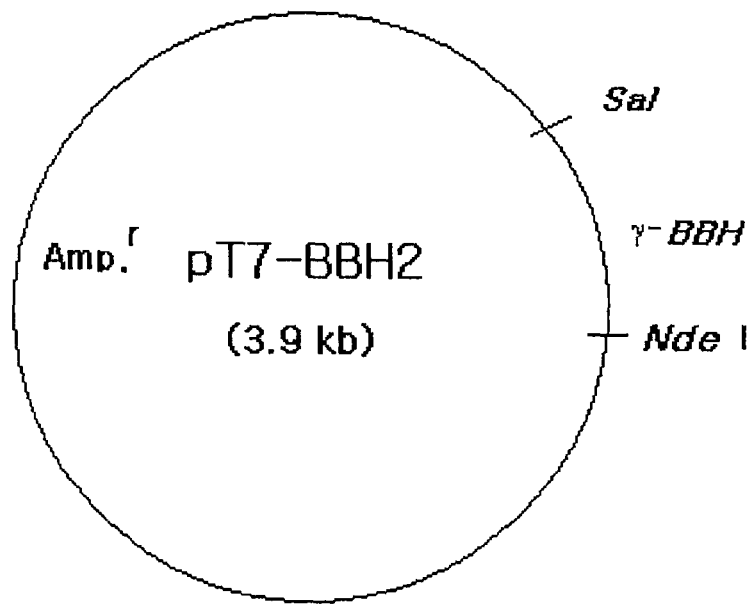
FIG. 4 is a schematic presentation of a pT7-BBH2 plasmid.

The obtained plasmid containing the γ-butyrobetaine hydroxylase gene was digested with NdeI and SalI, electrophoresed on a low-melting agarose gel. The DNA fragment corresponding to the γ-butyrobetaine hydroxylase gene was excised from the gel, purified, and inserted into pT7-7 treated with NdeI and SalI (FIG. 4). The resulting plasmid was transformed into *Escherichia coli* DH5 and grown on solid plates containing ampicillin. From emerged colonies, the recombinant plasmid was isolated. When the recombinant plasmid was digested with NdeI and SalI, the γ-BBH gene was found to have been successfully inserted into the plasmid (FIG. 2). Thus, the recombinant plasmid was designated as "pT7-BBH2". This recombinant plasmid was introduced into *Escherichia coli* DH5α. The resulting transformant was designated as "*Escherichia coli* BH5α CJ2004", which was deposited at the Korean Culture Center of Microorganisms (KCCM) on Jan. 27, 2004 and assigned accession number KCCM-10557.

EXAMPLE 5

Transformation of the pT7-BBH2 Plasmid into Expression Bacterial Strain *Escherichia coli* BL21(DE3)

The pT7-BBH2 plasmid possessing an ampicillin selection marker was transformed into an expression bacterial strain, *Escherichia coli* BL21(DE3). The *E. coil* BL21(DE3) strain produces T7 RNA polymerase in the presence of lactose or IPTG, which induces the translation of the γ-butyrobetaine hydroxylase gene. The transformed cells were smeared onto solid media containing ampicillin. From emerged colonies, the plasmid was purified and digested with NdeI and SalI to examine the size of the inserted gene and the plasmid. As a result, the pT7-BBH2 plasmid was found to have been successfully introduced into the *E. coli* strain BL21(DE3).

EXAMPLE 6

Expression of γ-butyrobetaine Hydroxylase

The transformant BL21(DE3)/pT7-BBH2, which was prepared in Example 5 by transforming the pT7-BBH2 plasmid into *E. coil* BL21(DE3), was cultured to evaluate the expression of γ-butyrobetaine hydroxylase. The transformant was cultured in a 250-ml baffle flask containing 50 ml of LB medium or LB medium supplemented with ampicillin. When the culture reached an OD600 value of 0.6, 1 mM IPTG was added to the medium, and the cells were further cultured for 4 hrs. The cells were harvested by centrifugation at 4,000×g for 15 min and resuspended in 1 ml of lysis buffer (140 mM NaCl, 200 g/liter glycerol, 1 mM DTT, 10 mM sodium phosphate buffer, pH 7.4,). The cell suspension was placed in ice and ultrasonicated for 10 sec five times using an ultrasonicator to disrupt cells. Then, the disrupted cells were centrifuged at 10,000×g for 20 to 30 min at 4° C. The supernatant was recovered, and the cell debris was discarded. SDS-PAGE analysis showed a band at about 49 kDa corresponding to the size of γ-butyrobetaine hydroxylase (FIG. 1). Protein concentrations were determined by the Bradford assay according to the intended use.

EXAMPLE 7

Measurement of L-carnitine

A crude extract of Neurospora crassa was incubated in 500 µl of assay buffer (20 mM KCl, 3 mM ketoglutarate, 10 mM sodium ascorbate, 2 g/liter Triton X-100, 0.25 mM $(NH_4)_2Fe(SO_4)_2$, 0.2 mM butyrobetaine, 20 mM potassium phosphate buffer, pH7.0) for 1 hr at 37° C. 500 µl of the supernatant of the extract was mixed with 500 µl of 1.2 M perchloric acid. The mixture was incubated for 10 min at room temperature and centrifuged for 5 min. 600 µl of the supernatant was mixed with 320 µl of 0.7 M $K_3PO_4$ and incubated in an ice bath for 20 min. After the mixture was centrifuged for 5 min, 750 µl of the supernatant was diluted in 250 µl of sterile distilled water. The diluted supernatant was supplemented with 100 µl of DNTB/$H_2O_2$ and incubated for 10 min at room temperature. Then, the reaction mixture was supplemented with 50 µl of a catalase solution, incubated at room temperature for 30 min, and centrifuged. 1 ml of the supernatant was mixed with 50 µl of acetyl CoA and incubated at room temperature for 10 min. Absorbance was measured at 405 nm and L-carnitine concentration was computed.

EXAMPLE 8

Evaluation of N. crassa-derived γ-butyrobetaine Hydroxylase for the Ability to Produce L-carnitine Using γ-butyrobetaine as a Substrate The E. coli strain BL21(DE3), transformed with the γ-butyrobetaine hydroxylase gene in Example 5, was cultured in a 250-ml baffle flask containing 50 ml of LB medium or LB medium supplemented with ampicillin. When the culture reached an OD600 value of 0.6, 1 mM IPTG was added to the medium, and the cells were cultured for over 8 hrs at 25° C. in order to prevent the formation of inclusion bodies while inducing the formation of accurate protein tertiary structure. Then, the cells were harvested by centrifugation at 4,000×g for 15 min, and a protein crude extract was prepared according to the same method as in Example 6. The crude extract containing 1.0 mg/ml proteins was incubated in a reaction buffer containing 0.5 mg/ml γ-butyrobetaine for 4 hrs. L-carnitine concentration was determined according to the same method as in Example 7, and the results are given in Table 1, below.

TABLE 1

| Assay mixture | L-carnitine Conc. (µg/ml) |
| --- | --- |
| γ-BBH assay buffer + 1.0 mg/ml BL21(DE3) crude extract | 0.0 |
| γ-BBH assay buffer + 1.0 mg/ml BL21(DE3)/pT7-BBH2 (induced by IPTG) crude extract | 0.8 |

INDUSTRIAL APPLICABILITY

As described hereinbefore, the novel gene encoding γ-butyrobetaine hydroxylase derived from Neurospora crassa is useful for producing optically pure L-carnitine from γ-butyrobetaine.

The invention claimed is:

1. An isolated polynucleotide comprising the nucleotide sequence of SEQ ID NO:1 encoding a γ-butyrobetaine hydroxylase.

2. An isolated recombinant vector comprising the polynucleotide of claim 1.

3. An isolated transformant transformed with the recombinant vector of claim 2.

4. The isolated transformant according to claim 3, wherein said transformant is *Escherichia coli*.

5. The isolated transformant according to claim 4, wherein said transformant is *Escherichia coli* DH5α CJ2004 having accession number KCCM-10557.

6. A method of preparing L-carnitine, comprising:
   a) cultivating the transformant of claim 4 in a culture medium;
   b) obtaining a protein crude extract comprising γ-butyrobetaine hydroxylase from the culture medium;
   c) incubating said protein crude extract and γ-butyrobetaine in a reaction buffer;
   d) collecting L-carnitine from the reaction buffer.

7. The method of preparing L-carnitine according to claim 6, wherein the transformant is *Escherichia coli* DH5α CJ2004 having accession number KCCM-10557.

* * * * *

UNITED STATES PATENT AND TRADEMARK OFFICE
CERTIFICATE OF CORRECTION

| | | |
|---|---|---|
| PATENT NO. | : 8,597,924 B2 | Page 1 of 1 |
| APPLICATION NO. | : 10/590831 | |
| DATED | : December 3, 2013 | |
| INVENTOR(S) | : Sung Oh Chung et al. | |

It is certified that error appears in the above-identified patent and that said Letters Patent is hereby corrected as shown below:

IN THE CLAIMS:

Col. 12, line 56-63

CLAIM 6 reads: "A method of preparing L-carnitine, comprising:
a) cultivating the transformant of claim 4 in a culture medium;
b) obtaining a protein crude extract comprising γ-butyrobetaine hydroxylase from the culture medium;
c) incubating said protein crude extract and γ-butyrobetaine in a reaction buffer;
d) collecting L-carnitine from the reaction buffer."

HOWEVER, IT SHOULD READ:

CLAIM 6: "A method of preparing L-carnitine, comprising:
a) cultivating the transformant of claim 4 in a culture medium;
b) obtaining a protein crude extract comprising γ-butyrobetaine hydroxylase from the culture medium;
c) incubating said protein crude extract and γ-butyrobetaine in a reaction buffer; and
d) collecting L-carnitine from the reaction buffer."

Signed and Sealed this
Twenty-second Day of April, 2014

Michelle K. Lee
*Deputy Director of the United States Patent and Trademark Office*

UNITED STATES PATENT AND TRADEMARK OFFICE
CERTIFICATE OF CORRECTION

PATENT NO.       : 8,597,924 B2                                              Page 1 of 1
APPLICATION NO.  : 10/590831
DATED            : December 3, 2013
INVENTOR(S)      : Chung et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1968 days.

Signed and Sealed this
Twenty-second Day of September, 2015

Michelle K. Lee
*Director of the United States Patent and Trademark Office*